US010591484B2

(12) United States Patent
Zhang et al.

(10) Patent No.: US 10,591,484 B2
(45) Date of Patent: Mar. 17, 2020

(54) ISOBARIC ALDEHYDE-REACTIVE TAGS FOR AND ANALYSIS OF GLYCANS USING SAME

(71) Applicants: THE JOHNS HOPKINS UNIVERSITY, Baltimore, MD (US); UNIVERSITY OF MARYLAND, COLLEGE PARK, College Park, MD (US)

(72) Inventors: Hui Zhang, Ellicott City, MD (US); Shuang Yang, Ellicott City, MD (US)

(73) Assignees: The Johns Hopkins University, Baltimore, MD (US); University of Maryland College Park, College Park, MD (US)

( * ) Notice: Subject to any disclaimer, the term of this patent is extended or adjusted under 35 U.S.C. 154(b) by 154 days.

(21) Appl. No.: 15/922,534

(22) Filed: Mar. 15, 2018

(65) Prior Publication Data

US 2018/0328931 A1 Nov. 15, 2018

Related U.S. Application Data

(62) Division of application No. 14/427,101, filed as application No. PCT/US2013/059057 on Sep. 10, 2013, now Pat. No. 9,939,444.

(Continued)

(51) Int. Cl.
*G01N 33/58* (2006.01)
*C08B 37/00* (2006.01)
(Continued)

(52) U.S. Cl.
CPC ........... *G01N 33/58* (2013.01); *C07C 237/22* (2013.01); *C08B 37/00* (2013.01); *G01N 33/50* (2013.01);
(Continued)

(58) Field of Classification Search
None
See application file for complete search history.

(56) References Cited

U.S. PATENT DOCUMENTS

2010/0256011 A1 10/2010 Hoffmann et al.
2010/0279269 A1 11/2010 Parsons et al.
2011/0207228 A1 8/2011 Sohn et al.

FOREIGN PATENT DOCUMENTS

EP 0462795 A2 12/1991

OTHER PUBLICATIONS

Yang, S., et al., "Glycan analysis by isobaric aldehyde reactive tag and mass spectrometry", Analytical Chemistry (2013) vol. 85, No. 17, pp. 8188-8195.

(Continued)

*Primary Examiner* — Xiaoyun R Xu
(74) *Attorney, Agent, or Firm* — John Hopkins Technology Ventures

(57) ABSTRACT

Highly specific and novel methods for analyzing glycans and proteoglycans are provided. The present invention provides glycan-reactive isobaric Aldehyde-Reactive Tags (iARTs) and the quantification of iARTs-labeled glycans by tandem mass spectrometry. The iARTs have an amine as an active group to react with aldehyde at the reducing end of glycans through reductive amination and demonstrated complete labeling. Due to the isobaric nature of the iARTs, differentially labeled glycans do not differ in mass, and quantitative information is provided by the isotope-encoded reporter ions generated from MS/MS or $MS^3$ spectra. Quantitative information is thus derived from signal of the reporter ions on same precursor. Uses of the information generated by the inventive methods for diagnosis and treatment are also disclosed.

3 Claims, 8 Drawing Sheets

Related U.S. Application Data

(60) Provisional application No. 61/699,178, filed on Sep. 10, 2012, provisional application No. 61/770,151, filed on Feb. 27, 2013.

(51) Int. Cl.
  *G01N 33/50* (2006.01)
  *C07C 237/22* (2006.01)
  *G01N 33/68* (2006.01)

(52) U.S. Cl.
  CPC ..... *G01N 33/6848* (2013.01); *G01N 2400/00* (2013.01); *G01N 2560/00* (2013.01); *Y10T 436/143333* (2015.01)

(56) References Cited

OTHER PUBLICATIONS

Ruhaak, L., et al., "Glycan labeling strategies and their use in identification and quantification", Analytical and Bioanalytical Chemistry (2010) vol. 397, pp. 3457-3481.

Tian, Y, et al., "Solid-phase extraction of N-linked glycopeptides", Nature Protocols (2007) vol. 2, No. 2, pp. 334-339.

Botelho, J., et al., "Quantification by isobaric labeling (QUIBL) for the comparative glycomic study of O-linked glycans" International Journal of Mass Spectrometry 278 (2008) 137-142.

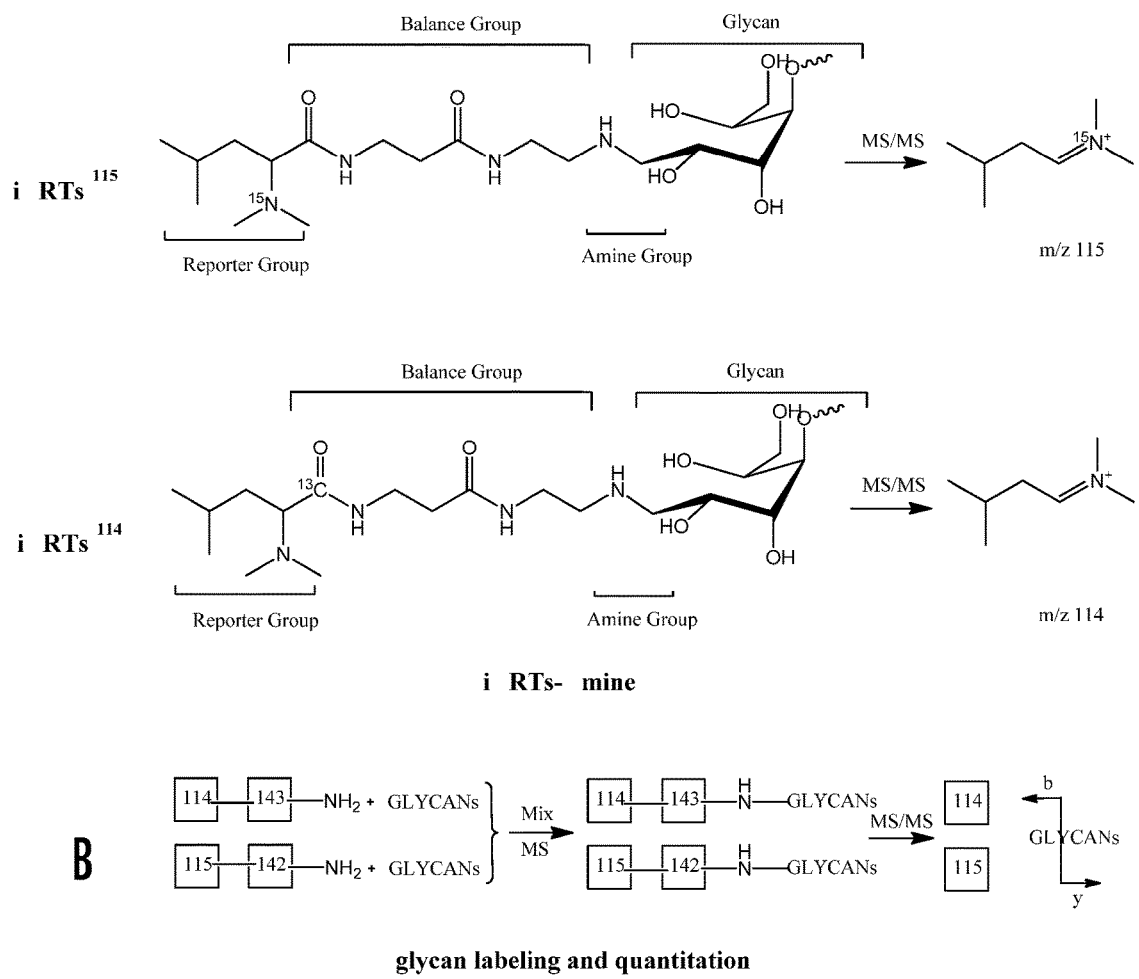
FIG. 3A-B

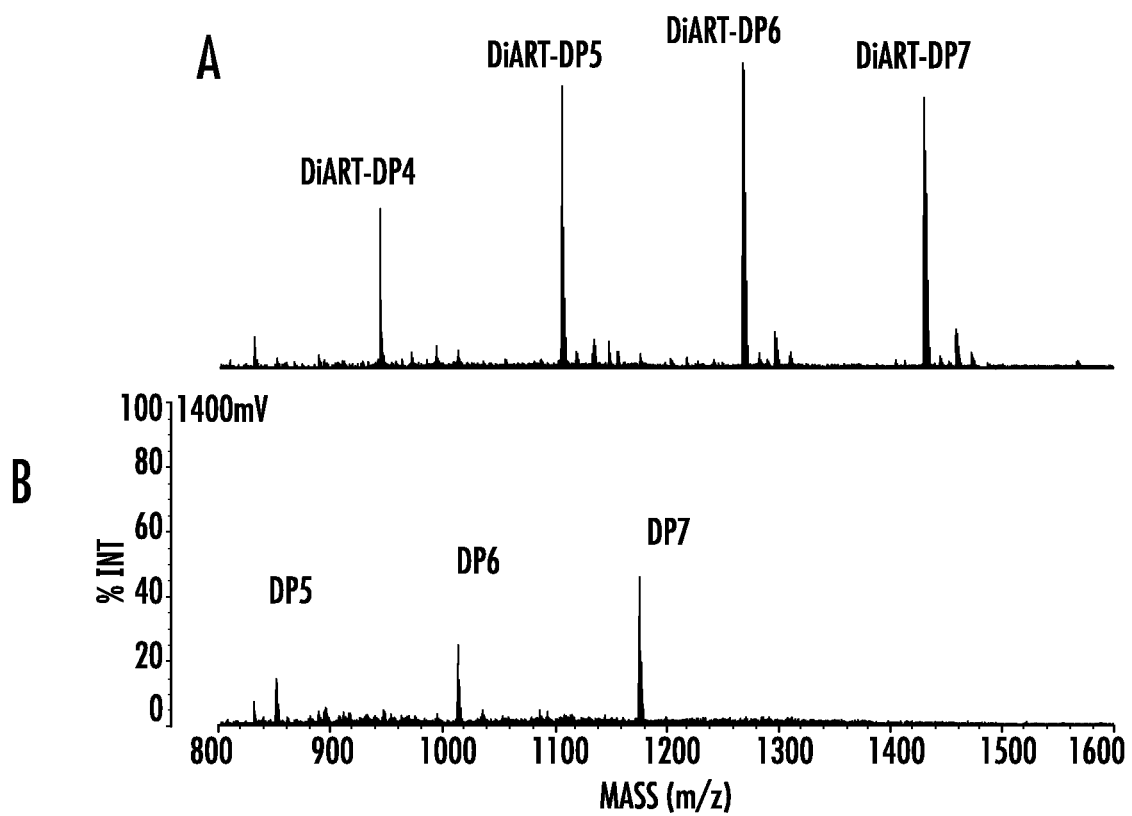
FIG. 4A-B

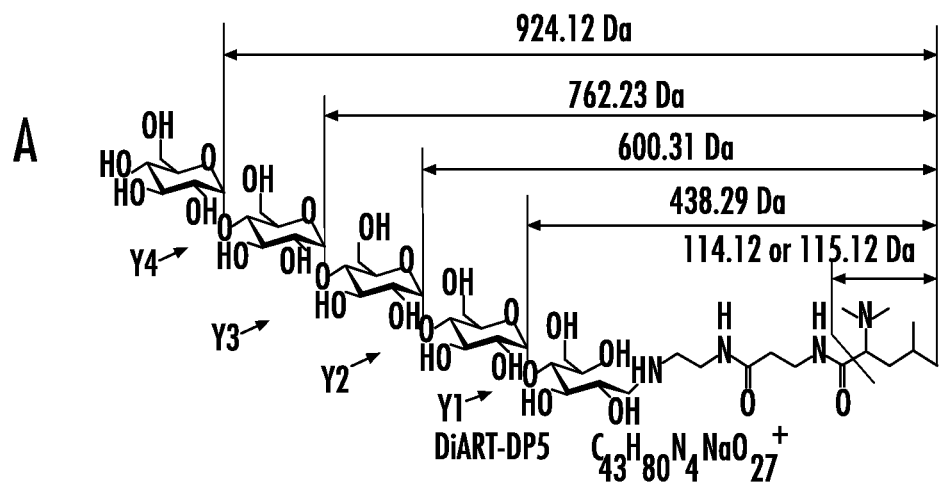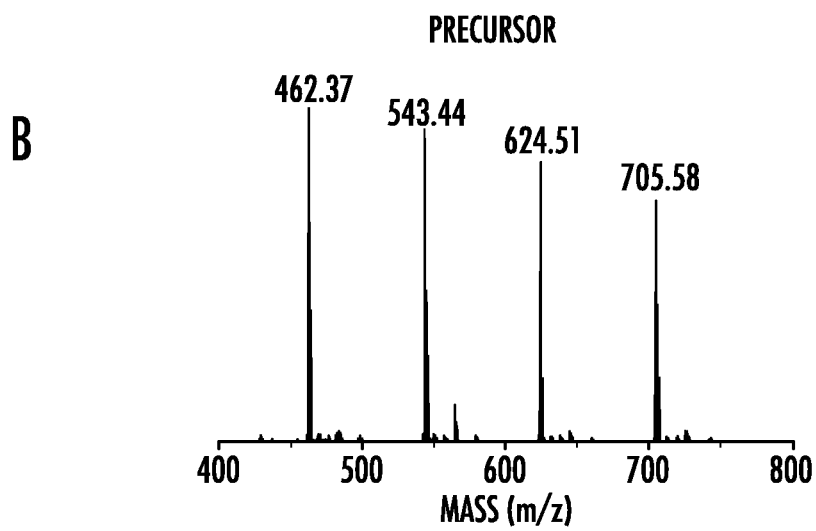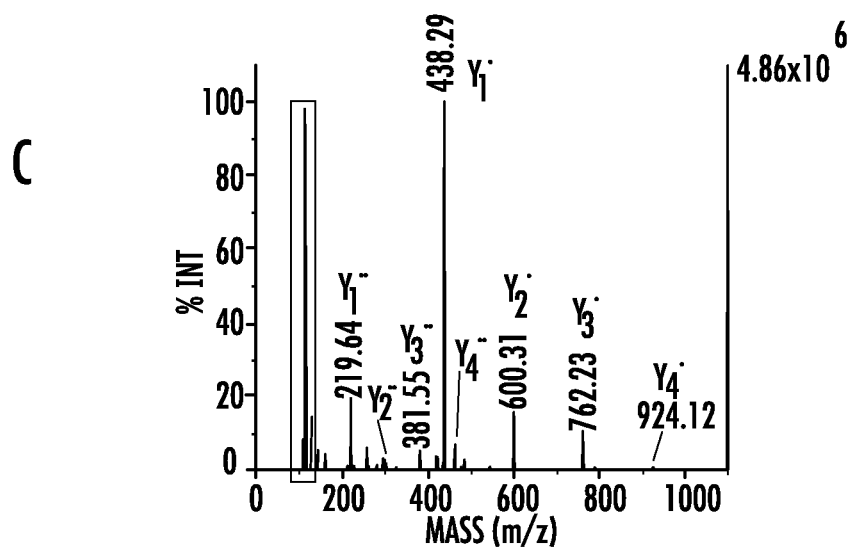
FIG. 5A-C

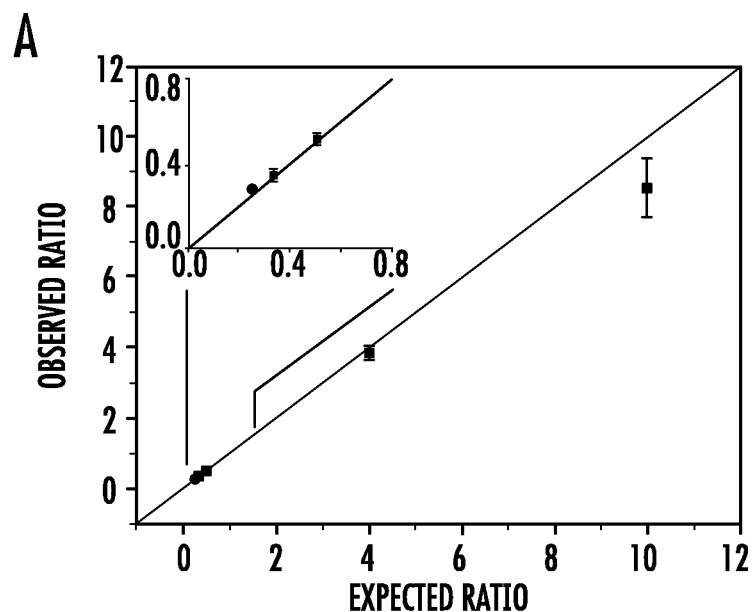
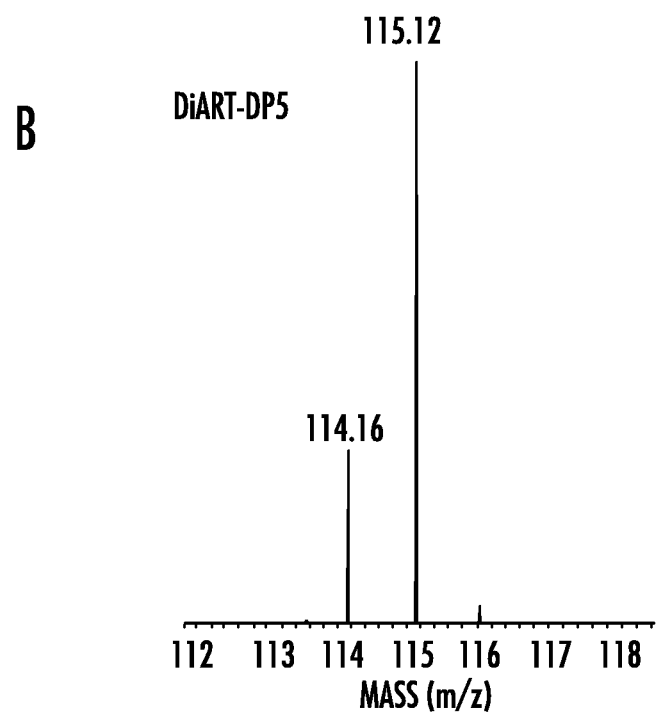
FIG. 6A-B

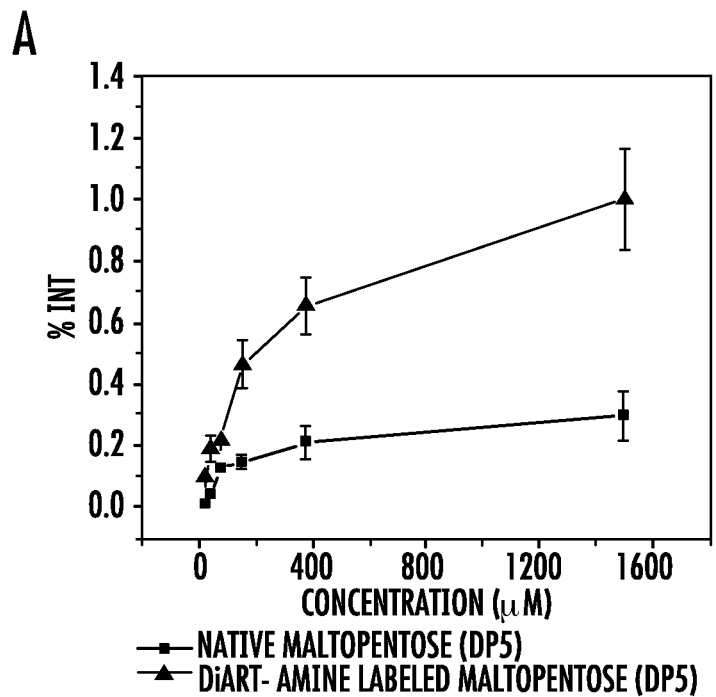
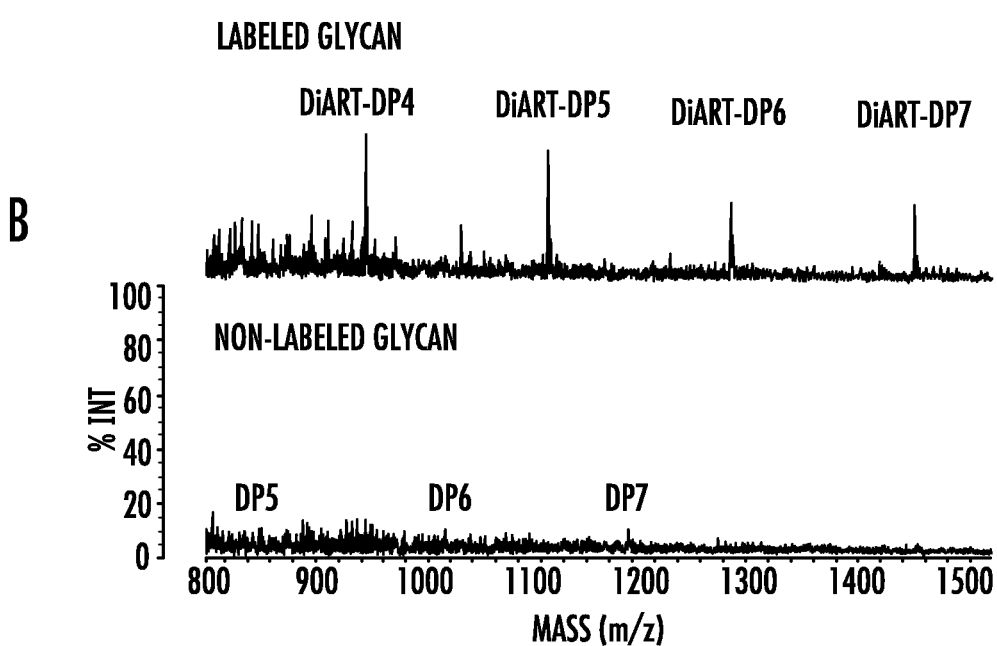
FIG. 7A-B

ISOBARIC ALDEHYDE-REACTIVE TAGS FOR AND ANALYSIS OF GLYCANS USING SAME

REFERENCE TO RELATED APPLICATIONS

This application is a Divisional of U.S. patent application Ser. No. 14/427,101, filed on Mar. 10, 2015, which is a 35 U.S.C. § 371 U.S. national entry of International Application PCT/US2013/059057, having an international filing date of Sep. 10, 2013, which claims the benefit of U.S. Provisional Application No. 61/699,178, filed Sep. 10, 2012, and U.S. Provisional Application No. 61/770,151, filed Feb. 27, 2013, the content of each of the aforementioned applications is herein incorporated by reference in their entirety.

STATEMENT OF GOVERNMENTAL INTEREST

This invention was made with government support under grant nos. CA152813 and HL107153 awarded by the National Institutes of Health. The government has certain rights in the invention.

BACKGROUND OF THE INVENTION

Protein glycosylation has been considered as one of the most significant protein modifications. It has been widely recognized that glycosylation is associated with disease progression, such as cancer, heart failure, and other congenital disorders. The investigation of glycoproteins and their associated glycans is the key to understanding glycoprotein functions in biological pathways and disease development as well as biomarker discovery. To this end, the present inventors previously developed the solid-phase extraction of glycopeptides (SPEG) for capture of glycosylated peptides, which has been widely applied to both quantitative analysis of glycoproteins and identification of glycosylation sites. In this method, glycosylated peptides from digested glycoproteins are captured by using hydrazide beads after glycans on glycopeptides are oxidized. Following the removal of non-glycosylated peptides, these glycosylated peptides are then enzymatically released from the solid support for mass spectrometry (MS) analysis. Using this method, thousands of new N-linked glycosylation sites have been identified. However, the glycans are removed from glycopeptides during the capture processes and their structures are not identified.

Quantitative and qualitative characterization of glycoprotein associated glycans is thus biologically significant. Many efforts have been devoted to derivatizing glycans at their reducing ends, on sialic acids, or permethylation of hydroxyl groups. Quantification by modifying glycans at their reducing ends with fluorescent tags has advantages including high sensitivity and high throughput, but the detection resolution is limited by front-end separation techniques. Stable isotope-coded tags have been developed and shown excellent resolution when combined with LC-MS analysis. Yet most isotope tags are mass-shift based, which may complicate spectra and lead to difficulty in data analysis. Isobaric tags, on the other hand, do not introduce more peaks on MS spectra and make it possible to analyze multiple samples concurrently.

Therefore, there still exists an unmet need to develop novel isotopic tags and analytical methods which can specifically isolate glycans or glycopeptides from complex mixtures, including biological and clinical samples.

SUMMARY OF THE INVENTION

In accordance with one or more embodiments, the present invention provides glycan-reactive isobaric Aldehyde-Reactive Tags (iARTs) and the quantification of iARTs-labeled glycans by tandem mass spectrometry. The iARTs have an amine as an active group to react with aldehyde at the reducing end of glycans through reductive amination and demonstrated complete labeling. Due to the isobaric nature of the iARTs, differentially labeled glycans do not differ in mass, and quantitative information is provided by the isotope-encoded reporter ions generated from MS/MS or $MS^3$ spectra. Quantitative information is thus derived from signal of the reporter ions on same precursor. A remarkable feature of the iARTs of the present invention, when compared to similar TMT and iTRAQ, is that reporter ions are much easier to fragment. Therefore, stronger reporter ions with better signal-to-noise can be obtained for accurate quantification from iARTs-labeled glycans.

In accordance with an embodiment, the present invention provides an iART ligand comprising: a) a reporter group comprising a $C_1$-$C_{10}$ to alkyl moiety having a primary amine group which can be optionally a $^{15}N$ labeled amine; b) a balance group consisting of —CONHCHCHCON-HCHCHNH—, wherein the first carbon can optionally be $^{13}C$; and when the amine is labeled, the first carbon is not labeled, and when the first carbon is labeled, the amine is not labeled, and said ligand can covalently linked to a glycan.

In accordance with an embodiment, the present invention provides a method for labeling glycans with iART ligands comprising: a) obtaining a sample of glycans isolated using solid-phase glycan extraction (SPGE) or solid-phase extraction of glycopeptides and glycans (SPEGAG); b) resuspending the glycans in a suitable solvent; c) dividing the denatured sample of b) into at least a first and second aliquots; d1) adding to the first aliquot, a sufficient quantity of a first iART; d2) adding to the second aliquot, a sufficient quantity of a second iART, wherein the molecular weight of the first iART and the second iART cannot be the same; e) heating the at least first and second aliquots for a sufficient time to conjugate the iARTs to the glycans in the at least first and second aliquots to make labeled glycans; and f) combining the at least first and second aliquots comprising the glycans labeled with the first and second iARTs and purifying the combined mixture.

In accordance with a further embodiment the present invention provides a method of generating a library comprising a glycans and glycopeptides using the above identified methods.

In accordance with still another embodiment, the present invention provides a method of detection and/or diagnosis of a disease or condition in a subject comprising generating a glycan or glycopeptide profile from a sample from the subject using the above identified methods, and comparing the glycan profile of the subject to a standard or normal profile and determining whether the subject has the disease or condition.

BRIEF DESCRIPTION OF THE DRAWINGS

FIG. 3A-3B depicts the structure of an embodiment of the iARTs of the present invention, and one strategy for quantitative analysis of glycans using iARTs labeling. (3A)

iARTs comprise three elements: a reporter group, a balance group, and a primary amine, which is used to covalently react with the reducing end of glycans through Schiff-base formation and reductive amination. (3B) Glycans from one sample are treated with light reagent (iARTs[114]), and glycans from another were treated with heavy reagent (iART[115]). The relative quantification is determined by the ratio of the reporter ions from tandem mass spectrometry.

FIG. 4A-4B are graphs depicting the complete labeling of glycans by iARTs. (4A) MALDI-MS spectra of complete labeled glycans (iART-DP4, -DP5, -DP6, -DP7). (4B) MALDI-MS spectra of native glycans (DP5, DP6, DP7). During labeling, the ratio of iARTs over glycans is 100-fold.

FIG. 5A-5C MS/MS shows a spectrum of iARTs labeled glycans. (5A) Structural illustration of reporters (114 or 115) and glycan pattern (Y ions) observed in MS/MS spectra. (5B) Doubly positive-charged iARTs-glycans (DP4, DP5, DP6, DP7) detected by HCD-Orbitrap. (5C) A representative MS/MS spectrum of iARTs glycans acquired in Orbitrap (iARTs-DP5). Fragments consist of Y-ions with one- or two-charge.

FIG. 6A-6B depicts the dynamic range and accuracy of iARTs quantitation of glycans (6A). Glycans were mixed in known ratios (1:4, 1:3, 1:2, 4:1, and 10:1; 114/115) in which each experiment was analyzed in triplicate. Insert shows the linearity of glycan labeling from 1:4 to 1:2. (6B) MS/MS reporter ion of glycans with expected ratio of 1:3 (114/115).

FIG. 7A-7B shows the improvement of glycan ionization efficiency by iARTs isobaric labeling. (7A) Signal enhancement of iARTs labeled DP5 over native DP5. (7B) MALDI-MS spectra of labeled and native glycans (DP6, 25 µM). Sensitivity of labeled glycans increases up to 10 fold.

Figure 8:
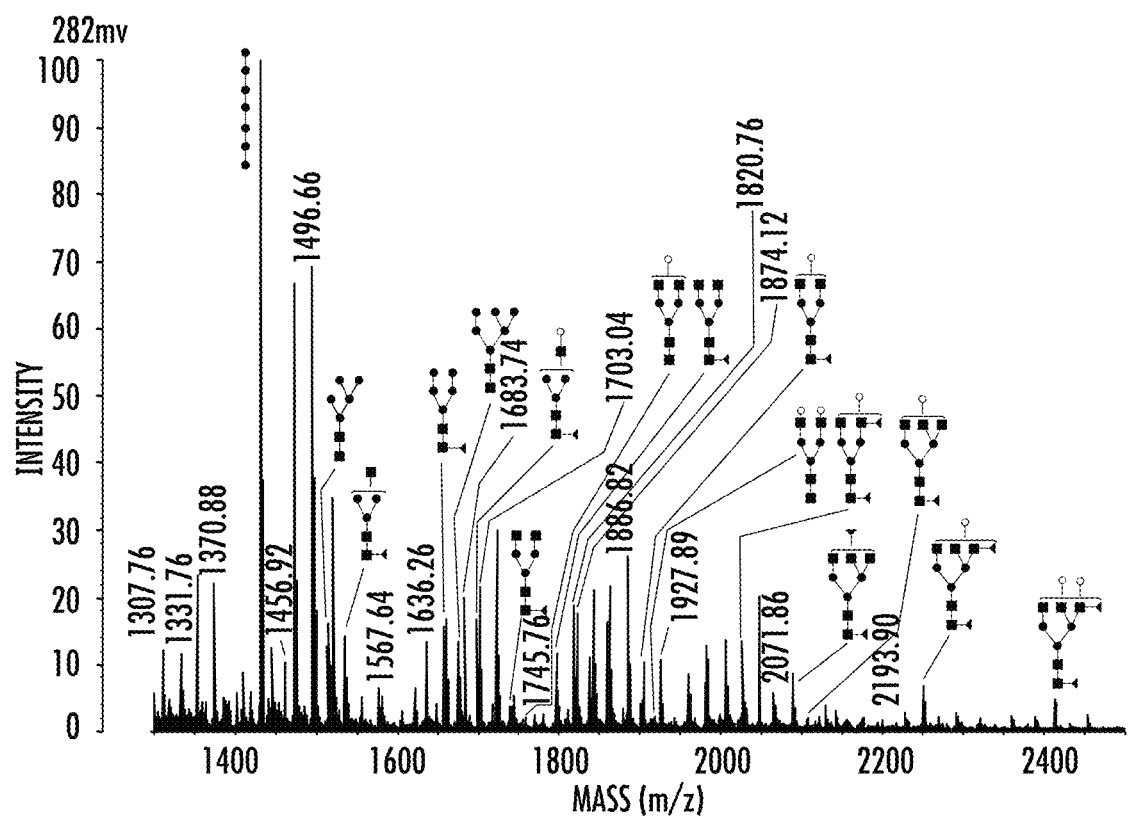

FIG. 8 depicts identified iARTs-glycans from gp120 by SPGE-MALDI-MS/MS. Glycans further labeled with iARTs in DMSO-acetic acid in the presence of 50 mM sodium borocyanohydride.

DETAILED DESCRIPTION OF THE INVENTION

Methods are provided herein which are directed to improved methods of analyzing carbohydrates. As used herein, the term "carbohydrate" is intended to include any of a class of aldehyde or ketone derivatives of polyhydric alcohols. Therefore, carbohydrates include starches, celluloses, gums and saccharides. Although, for illustration, the term "saccharide" or "glycan" is used below, this is not intended to be limiting. It is intended that the methods provided herein can be directed to any carbohydrate, and the use of a specific carbohydrate is not meant to be limiting to that carbohydrate only.

As used herein, the term "saccharide" refers to a polymer comprising one or more monosaccharide groups. Saccharides, therefore, include mono-, di-, tri- and polysaccharides (or glycans). Glycans can be branched or branched. Glycans can be found covalently linked to non-saccharide moieties, such as lipids or proteins (as a glycoconjugate). These covalent conjugates include glycoproteins, glycopeptides, peptidoglycans, proteoglycans, glycolipids and lipopolysaccharides. The use of any one of these terms also is not intended to be limiting as the description is provided for illustrative purposes. In addition to the glycans being found as part of a glycoconjugate, the glycans can also be in free form (i.e., separate from and not associated with another moiety). The use of the term peptide is not intended to be limiting. The methods provided herein are also intended to include proteins where "peptide" is recited.

The novel iARTs and their methods of use as labels for glycans, can be used with glycans purified from samples containing glycoproteins and/or glycopeptides. Suitable methods of isolating an purifying the glycans to be quantified using the inventive methods are known in the art. In some embodiments the glycans are purified using Solid-Phase Glycan Extraction (SPGE). Proteins or peptides are immobilized on a solid support, other molecules were removed, and glycans are then released from glycoproteins/glycopeptides for analysis by mass spectroscopy. The methods can be applied to the analysis of glycans from human serum and cells. The isolated glycans can be labeled with the iARTs of the present invention for quantitative analysis.

SPGE has a number of advantages for glycan analysis. First, specific glycans can be directly analyzed without further purification. This results in high yields from the glycan isolation and high sensitivity of detection and also reduced time and cost by eliminating traditional glycan purification steps using C-18 and graphite columns. Second, the solid-phase capture method provides a platform for glycan modifications using enzymes or chemicals.

The enzymes and chemicals can be easily removed and other reagents added providing a specific and rapid method for glycan modification or derivatization from complex samples. The SPGE procedure is quantitative and the isolated glycans are compatible with current downstream analytical platforms. In the present invention, the isolated glycans were analyzed by MS using label-free quantification, although the method could be used with stable-isotopic labeling of glycans to obtain accurate quantitation. Glycans can also be labeled with fluorescence tags for chromatography or electrophoresis analyses.

Figure 1:
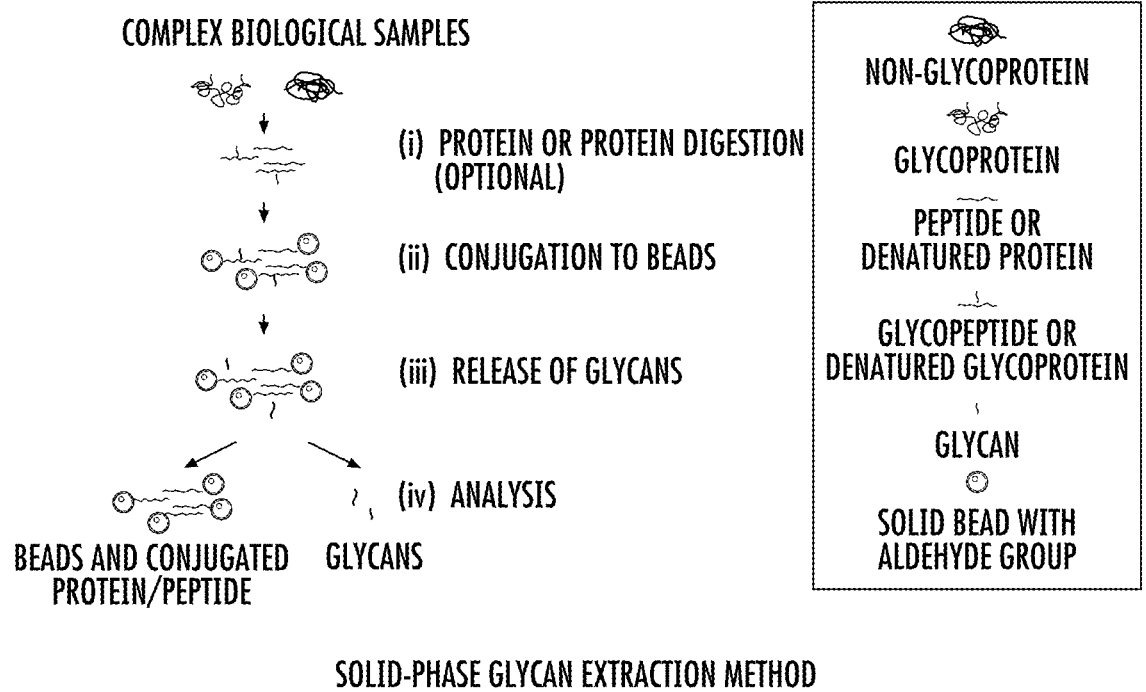
FIG. 1 is a schematic diagram of glycan capture and release using the SPGE method.

SPGE is detailed in U.S. Provisional Patent Application Nos. 61/699,178, and 61/770,151, and are incorporated by reference herein in their entireties, and a schematic of the procedure is shown in FIG. 1. Briefly, Both N-linked and O-linked glycoproteins are conjugated to a solid support (AminoLink beads, for example) through reductive amination. N-glycans can be specifically released from the solid support by PNGase F. After releasing N-glycans, O-glycans can be released from beads for analysis. However, there is no enzyme comparable to PNGase F for removing intact O-linked glycans. To successfully release O-linked oligosaccharides, it is necessary to sequentially remove monosaccharides by using a panel of exoglycosidases until only the Galβ1,3GalNAc core remains attached to the serine or threonine residue. The core can then be released by O-glycosidase. Since not all O-linked oligosaccharides contain this core structure, a chemical method, such as β-elimination may be more general and effective for the release of the formerly O-linked glycosylated peptides. The solid-phase capture of proteins is also likely to provide a powerful platform to study other protein post-translational modifications, such as acylation, phosphorylation, and ubiquitination.

Figure 2:
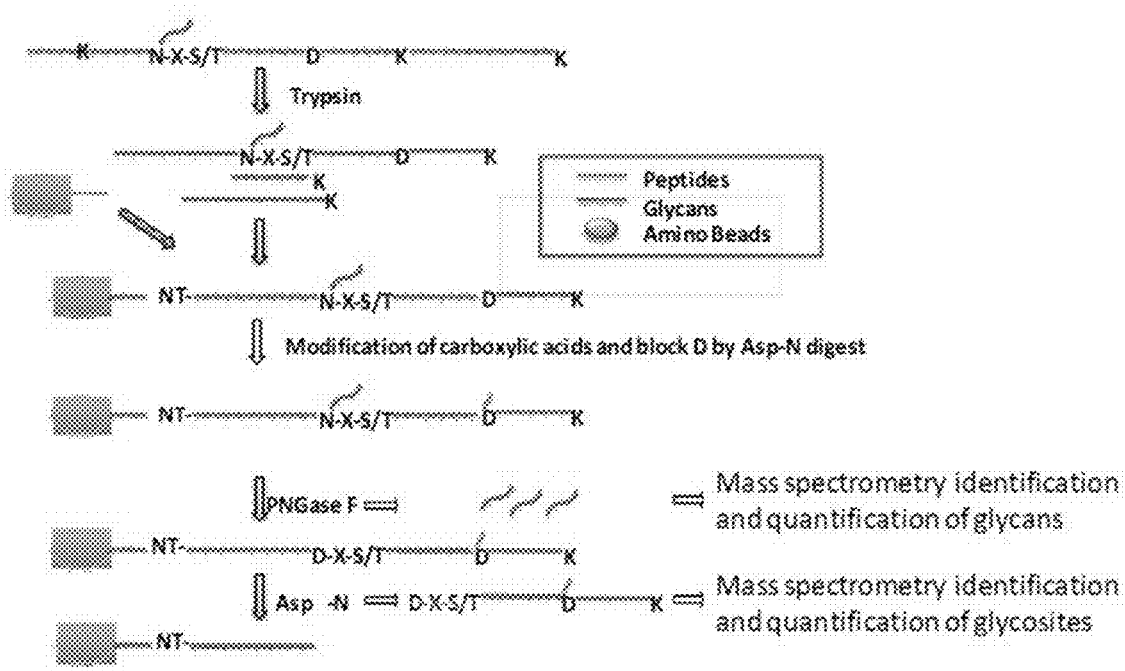
FIG. 2 is a schematic of SPEGAG method which can be used in the methods of the present invention.

In accordance with some embodiments, the glycans can be purified from a sample using the SPEGAG method of the present inventors, which is also detailed in the provisional patent applications disclosed above. A representative example is shown as follows. The method for solid-phase extraction of glycopeptides and glycans SPEGAG method was applied to the analysis of human serum with the following steps (FIG. 2): 1; 1 mg human serum was digested by trypsin overnight; 2. The sample was cleaned up with a C18 cartridge using standard methods; 3. Guanidylation (Translate Lysine to Homoarginine), the sample is guanidinylated using standard protocol; 4. The sample was cleaned up with a C18 cartridge using standard methods; 5. The peptide mixture is then coupled to a solid support by reductive amination in PBS buffer, pH7.4 with 50 mM NaCNBH3; 6. Blocking unused aldehyde groups on the solid support; 7. Labeling the acid groups by aniline. (add internal standard peptides to check label efficiency). The labeling can be isotopic or isobaric tags to introduce mass difference for glycan and glycopeptide quantification; 8. An Asp-N digest of the sample is then performed to remove any unlabeled aspartic acid groups; 9. The samples are then digested with PNGase F to release N-glycans from the substrate; 10. The released glycans can be optionally labeled by iARTs; 11. Analyzing the released glycans by MS to identify and quantify glycans; 12. Digesting the peptides on the solid substrate with Asp-N to release N-glycopeptides at the N-terminal of the glycosylation motif (▼NXT/S); 13. Analyzing the released glycans by MS to identify and quantify glycans; 14.

Search LC-MS/MS against database: for example, ipi.HUMAN.v3.87N_KN.fasta (all N-X-S/T were replaced by K-N-X-S/T so that I could select trypsin as enzyme) using the following parameters:

Enzyme Name: Trypsin (Full) Maximum Missed Cleavage Sites: 1
Using dynamic Modifications: Max. Modifications Per Peptide: 7
C-Terminal Modification: AnilineCtermi/+75.047 Da (Any C-Terminus)
1. Dynamic Modification: Deamidated/+0.984 Da (N)
2. Dynamic Modification: Guanidinyl/+42.022 Da (K) Modify Lysine to HomoArginine
3. Dynamic Modification: Oxidation/+15.995 Da (M)
4. Dynamic Modification: AnilineDE/+75.047 Da (D, E)
5. Dynamic Modification: Guanidylaniline/+117.069 Da (K)
5. Static Modifications:
1. Static Modification: Carbamidomethyl/+57.021 Da (C)
Target FDR (Relaxed): 0.05

In accordance with an embodiment, the present invention provides the preparation of glycan-reactive isobaric Aldehyde-Reactive Tags (iARTs) and their use in methods for the quantification of iARTs-labeled glycans by tandem mass spectrometry. Glycans were labeled with iARTs by reductive amination at their reducing ends. It was found that the iARTs labeling not only allowed the quantification of glycans, but also increased ionization efficiency by enhancing their hydrophobicity. The modification at the single reducing end of each native glycan gives the precise mass difference for glycans from different samples during MS/MS analysis without complicating the MS. In conjugation with glycan preparation by solid-phase glycan extraction, the method was applied to the quantitative analysis of glycans from gp120 glycoprotein in human immunodeficiency virus (HIV).

In accordance with another embodiment of the present invention, it will be understood that the term "biological sample" or "biological fluid" includes, but is not limited to, any quantity of a substance from a living or formerly living subject. Such substances include, but are not limited to, blood, serum, plasma, urine, cells, organs, tissues, bone, bone marrow, lymph, lymph nodes, synovial tissue, CSF, chondrocytes, synovial macrophages, endothelial cells, and skin. In a preferred embodiment, the fluid is blood or serum.

As used herein, the term "subject" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

It will be understood by those of skill in the art that the denaturation of the glycoproteins in the sample, in the inventive methods, can be accomplished using any means known in the art. In addition to heating, denaturation agents and proteolysis may also be used. A "denaturing agent" is an agent that alters the structure of a molecule, such as a protein. Denaturing agents, therefore, include agents that cause a molecule, such as a protein to unfold. Denaturing can be accomplished, for instance, with heat, with heat denaturation in the presence of β-mercaptoethanol and/or SDS, by reduction followed by carboxymethylation (or alkylation), etc. Reduction can be accomplished with reducing agent, such as, dithiothreitol (DTT). Carboxymethylation or alkylation can be accomplished with, for example, iodoacetic acid or iodoacetamide. Denaturation can, for example, be accomplished by reducing with DTT, β-mercaptoethanol or tri(2-carboxyethyl)phosphine (TCEP) followed by carboxymethylation with iodoacetic acid. When the glycoconjugate sample is a sample of a body fluid, such as serum, the denaturation can be accomplished with EndoF. The glycoconjugates can also be denatured with denaturing agents, such as detergent, urea or guanidium hydrochloride.

In accordance with an embodiment, the methods of analyzing glycans of the present invention includes cleaving the glycans from the glycoconjugates using any chemical or enzymatic methods or combinations thereof that are known in the art. An example of a chemical method for cleaving glycans from glycoconjugates is hydrazinolysis or alkali borohydrate. Enyzmatic methods include methods that are specific to N- or O-linked sugars. These enzymatic methods include the use of Endoglycosidase H (Endo H), Endoglycosidase F (EndoF), N-Glycanase F (PNGaseF) or combinations thereof. In some preferred embodiments, PNGaseF is used when the release of N-glycans is desired. When PNGaseF is used for glycan release the proteins is, for example, first unfolded prior to the use of the enzyme. The unfolding of the protein can be accomplished with any of the denaturing agents provided above.

In accordance with an embodiment of the above methods of the present invention the denaturing of the sample in a) comprises: i) heating the sample for a sufficient period of time; ii) incubating the sample from i) with a proteolytic enzyme for a period of time; and iii) adding a sufficient amount of PNGase F to the sample of ii) to release the glycans from the peptide fragments.

It is understood by those of skill in the art that the proteolytic enzyme used in the inventive methods can be any enzyme capable of cleaving peptide bonds. Examples of proteolytic enzymes useful in the inventive methods include trypsin, chymotrypsin, papain, and pepsin.

After protein denaturation and/or digestion, the (If using Endo H, the peptide portion still containing carbohydrate) peptides and protein fragments can be removed by washing or use of various column based methods known in the art. Alternatively, the peptides and protein fragments can be collected and separately analyzed using known methods.

In accordance with a further embodiment, the conjugation of the released glycans to the solid support is performed in the absence or presence of a catalyst. It will be understood by those of skill in the art that catalysts suitable for use with the methods of the present invention will include those compounds that can act as a Schiff-base intermediate in the reaction of the free reducing ends of the glycans with the hydrazide moieties on the solid support. In the inventive methods, the catalyst can be added to the mixture of the released glycans and solid support. In accordance with an embodiment, the catalyst used in the inventive methods is aniline.

The solid substrate used to bind the glycans and glycopeptides in the inventive methods may be a material that may be modified to contain discrete individual sites appropriate for the attachment or association of the glycans and is amenable to at least one detection method. Representative examples of substrates include glass and modified or functionalized glass, plastics (including acrylics, polystyrene and copolymers of styrene and other materials, polypropylene, polyethylene, polybutylene, polyurethanes, Teflon, etc.), polysaccharides, nylon or nitrocellulose, resins, silica or silica-based materials including silicon and modified silicon, carbon, metals, inorganic glasses and plastics.

In an alternative embodiment, other supports, such as slides, for example can be used as the solid support. This is particularly useful for glycan analysis with spatial information and can be applied to glycan imaging of tissues. In yet another embodiment tags can also be used in place of solid supports, using well known ligands such as biotin-hydrazide or azido-hydrazide, that can be used to conjugate the glycans in solution and then are subsequently captured using the tags. This solution capture embodiment is particularly useful to capture glycans in vivo.

After the removal of the non-conjugated components, the glycans or glycopeptides (both N- and O-glycopeptides) can be released from beads by hydrolysis and analyzed using the iARTs of the present invention. In accordance with an embodiment, the hydrolysis of the hydrazone bonds is accomplished by lowering the pH of the solution to <3. In some embodiments the range of pH is between about pH 1 to about pH 3, preferably about pH 2. While it will be understood that any acid solution can be used to accomplish this, such as, for example trifluoroacetic acid (<1% v/v), 0.01 M HCl, or 0.005 M $H_2SO_4$. In accordance with an embodiment, 10% v/v formic acid is suitable for this use.

Therefore, in accordance with some embodiments, the present invention provides a method for labeling glycans with iART ligands comprising: a) obtaining a sample of glycans isolated using SPEG or SPEGAG; b) resuspending the glycans in a suitable solvent; c) dividing the denatured sample of b) into at least a first and second aliquots; d1) adding to the first aliquot, a sufficient quantity of a first iART; d2) adding to the second aliquot, a sufficient quantity of a second iART, wherein the molecular weight of the first iART and the second iART cannot be the same; e) heating the at least first and second aliquots for a sufficient time to conjugate the iARTs to the glycans in the at least first and second aliquots to make labeled glycans; and f) combining the at least first and second aliquots comprising the glycans labeled with the first and second iARTs and purifying the combined mixture.

In some embodiments, the iARTs used can be iART[114] and iART[115].

In accordance with some embodiments the glycans can be labeled with iARTs at a ratio of iART to glycan at 1:1, 2:1, 5:1, 10:1, 20:1, 50:1, 100:1, up to about 500:1. In a preferred embodiment, the glycans can be labeled with iARTs at a ratio of iART to glycan of at least 100:1 or greater.

In accordance with an embodiment, the step of analyzing the glycans includes, in certain embodiments, analyzing the glycans with a mass spectrometric method, an electrophoretic method, NMR, a chromatographic method or a combination thereof. In a further embodiment, the mass spectrometric method is LC-MS and LC-MS/MS using LC-Orbitrap, LC-FTMS, LC-LTQ, MALDI-MS including but not limited to MALDI-TOF, MALDI-TOF/TOF, MALDI-qTOF, and MALDI-QIT. Preferably, the mass spectrometric method is a quantitative MALDI-MS or LC-MS using optimized conditions. In still another embodiment, the electrophoretic method is CE-LIF. In yet another embodiment, methods such as capillary gel electrophoresis or capillary zone electrophoresis can be used with the inventive methods.

In other embodiments, includes quantifying the glycans using calibration curves of known glycan standards.

In yet another embodiment, the methods of the present invention include a method for diagnostic or prognostic purposes.

In a further embodiment, the methods of the present invention include a method for assessing the purity of the sample.

In some embodiments, the methods are methods of diagnosis and the pattern is associated with a diseased state. In one preferred embodiment, the pattern associated with a diseased state is a pattern associated with cancer, such as prostate cancer, melanoma, bladder cancer, breast cancer, lymphoma, ovarian cancer, lung cancer, colorectal cancer or head and neck cancer. In other preferred embodiments, the pattern associated with a diseased state is a pattern associated with an immunological disorder; a neurodegenerative disease, such as a transmissible spongiform encephalopathy, Alzheimer's disease or neuropathy; inflammation; rheumatoid arthritis; cystic fibrosis; or an infection, preferably viral or bacterial infection. In other embodiments, the method is a method of monitoring prognosis and the known pattern is associated with the prognosis of a disease.

In yet another embodiment, the method is a method of monitoring drug treatment and the known pattern is associated with the drug treatment. In particular, the methods (e.g., analysis of glycome profiles) are used for the selection of population-oriented drug treatments and/or in prospective studies for selection of dosing, for activity monitoring and/or for determining efficacy endpoints.

Methods of analyzing glycans of glycoconjugates can also include cleaving the glycans from glycoconjugates using any chemical or enzymatic methods or combinations thereof that are known in the art. An example of a chemical method for cleaving glycans from glycoconjugates is hydrazinolysis or alkali borohydrate. Enyzmatic methods include methods that are specific to N- or O-linked sugars. These enzymatic methods include the use of Endoglycosidase H (Endo H), Endoglycosidase F (EndoF), N-Glycanase F (PNGaseF) or combinations thereof. In some preferred embodiments, PNGaseF is used when the release of N-glycans is desired. When PNGaseF is used for glycan release the proteins is, for example, first unfolded prior to the use of the enzyme. The unfolding of the protein can be accomplished with any of the denaturing agents provided above.

After the release of the glycan from the protein core, or when the glycans were already in free form (not part of a glycoconjugate), the sample can be purified, for instance, by precipitating the proteins with ethanol and removing the supernatant containing the glycans. Other experimental methods for removing the proteins, detergent (from a denaturing step) and salts include any methods known in the art. These methods include dialysis, chromatographic methods, etc. In one example, the purification is accomplished with a porous graphite column. In some preferred embodiments, everything but the glycans is removed from the sample. Samples can also be purified with commercially available resins and cartridges for clean-up after chemical cleavage or enzymatic digestion used to separate glycans from protein. Such resins and cartridges include ion exchange resins and purification columns, such as GlycoClean H, S, and R cartridges. Preferably, in some embodiments GlycoClean H is used for purification.

Purification can also include the removal of high abundance proteins, such as the removal of albumin and/or antibodies, from a sample containing glycans. In some methods the purification can also include the removal of unglycosylated molecules, such as unglycosylated proteins. Removal of high abundance proteins can be a desirable step for some methods, such as some high-throughput methods described elsewhere herein. In some embodiments of the methods provided, abundant proteins, such as albumin or antibodies, can be removed from the samples prior to the final composition analysis.

Any analytic method for analyzing the glycans so as to characterize them can be performed on any sample of glycans, such analytic methods include those described herein. As used herein, to "characterize" a glycan or other molecule means to obtain data that can be used to determine its identity, structure, composition or quantity. When the term is used in reference to a glycoconjugate, it can also include determining the glycosylation sites, the glycosylation site occupancy, the identity, structure, composition or quantity of the glycan and/or non-saccharide moiety of the glycoconjugate as well as the identity and quantity of the specific glycoform. These methods include, for example, mass spectrometry, NMR (e.g., 2D-NMR), electrophoresis and chromatographic methods. Examples of mass spectrometric methods include FAB-MS, LC-MS, LC-MS/MS, MALDI-MS, MALDI-MS/MS, etc. NMR methods can include, for example, COSY, TOCSY, NOESY. Electrophoresis can include, for example, CE-LIF, CGE, CZE, COSY, TOCSY, NOESY. Electrophoresis can include, for example, CE-LIF.

The library consists of free or labeled glycoconjugates and fragments of the glycoconjugates, the fragments being the non-saccharide portions of the glycoconjugates. In one example, a library is generated from a sample, by isolating the glycoconjugates or free glycans or by cleaving the backbone of the glycoconjugates in the sample. The glycans or glycoconjugates can then be removed from the sample. The libraries so produced can be analyzed with the methods provided herein. The libraries can also be used as a standard once characterized and methods of using such libraries are also provided.

In one embodiment, the inventive methods include a method of analyzing a sample with glycoconjugates includes isolating free forms of glycans or glycoconjugate, or cleaving the glycoconjugates by enzymatically or chemically removing the glycans from the glycoconjugates and mixing the sample with a standard. The sample mixed with the standard can then be analyzed. In one embodiment, the amounts of the glycoconjugates and non-saccharide moieties of the sample and standard are compared. In one aspect of the invention the standards are also provided.

Prior to analysis of the sample, the sample can also be degraded with a chemical or enzymatic method to cleave the glycans from any glycoconjugates in the sample. Examples of enzymatic methods are provided above and include, for example, the use of PNGase F, endoglycosydase H and endoglycosydase F or combinations thereof. Chemical methods have also been described above and include hydrazinolisis, alkali borohydrate or beta-elimination.

As stated above, the glycosylation of a protein may be indicative of a normal or a disease state. Therefore, methods are provided for diagnostic purposes based on the analysis of the glycosylation of a protein or set of proteins, such as the total glycome. The methods provided herein can be used for the diagnosis of any disease or condition that is caused or results in changes in a particular protein glycosylation or pattern of glycosylation. These patterns can then be compared to "normal" and/or "diseased" patterns to develop a diagnosis, and treatment for a subject. For example, the methods provided can be used in the diagnosis of cancer, inflammatory disease, benign prostatic hyperplasia (BPH), etc.

The diagnosis can be carried out in a person with or thought to have a disease or condition. The diagnosis can also be carried out in a person thought to be at risk for a disease or condition. "A person at risk" is one that has either a genetic predisposition to have the disease or condition or is one that has been exposed to a factor that could increase his/her risk of developing the disease or condition.

Detection of cancers at an early stage is crucial for its efficient treatment. Despite advances in diagnostic technologies, many cases of cancer are not diagnosed and treated until the malignant cells have invaded the surrounding tissue or metastasized throughout the body. Although current diagnostic approaches have significantly contributed to the detection of cancer, they still present problems in sensitivity and specificity.

In accordance with one or more embodiments of the present invention, it will be understood that the types of cancer diagnosis which may be made, using the methods provided herein, is not necessarily limited. For purposes herein, the cancer can be any cancer. As used herein, the term "cancer" is meant any malignant growth or tumor caused by abnormal and uncontrolled cell division that may spread to other parts of the body through the lymphatic system or the blood stream.

The cancer can be a metastatic cancer or a non-metastatic (e.g., localized) cancer. As used herein, the term "metastatic cancer" refers to a cancer in which cells of the cancer have metastasized, e.g., the cancer is characterized by metastasis of a cancer cells. The metastasis can be regional metastasis or distant metastasis, as described herein.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of diagnosis, staging, screening, or other patient management, including treatment or prevention of cancer in a mammal. Furthermore, the treatment or prevention provided by the inventive method can include treatment or prevention of one or more conditions or symptoms of the disease, e.g., cancer, being treated or prevented. Also, for purposes herein, "prevention" can encompass delaying the onset of the disease, or a symptom or condition thereof.

In accordance with an embodiment, the present invention provides a use of a glycan profile prepared using the method disclosed herein to diagnose a disease or condition in a subject, comprising comparing the glycan profile from a subject to a glycan profile from a normal sample, or diseased sample, and determining whether the sample of the subject has the disease or condition.

In accordance with the inventive methods, the terms "cancers" or "tumors" also include but are not limited to adrenal gland cancer, biliary tract cancer; bladder cancer, brain cancer; breast cancer; cervical cancer; choriocarcinoma; colon cancer; endometrial cancer; esophageal cancer; extrahepatic bile duct cancer; gastric cancer; head and neck cancer; intraepithelial neoplasms; kidney cancer; leukemia; lymphomas; liver cancer; lung cancer (e.g. small cell and non-small cell); melanoma; multiple myeloma; neuroblastomas; oral cancer; ovarian cancer; pancreas cancer; prostate cancer; rectal cancer; sarcomas; skin cancer; small intestine cancer; testicular cancer; thyroid cancer; uterine cancer; urethral cancer and renal cancer, as well as other carcinomas and sarcomas.

EXAMPLES iART Materials and Reagents

Concentrated denaturing buffer consists of 400 mM Dithiothreitol (DTT) and 5% sodium dodecyl sulfate (SDS) (New England BioLabs; Ipswich, Mass.). Peptide-N-glycosidase F (PNGase F) was from New England BioLabs. Both snap-cap spin-column and AminoLink resin were from Pierce (Thermo Scientific; Rockford, Ill.). μ-Focus MALDI plate (Hudson Surface Technology; Fort Lee, N.J.) was amounted to Shimadzu adapter for glycan identification by AXIMA Resonance MALDI-QIT-TOF MS (Shimadzu Corporation; Columbia, Md.). HPLC-grade solvents, including high-performance liquid chromatography (HPLC) grade water, acetonitrile (99.9%), methanol (99.9%), ethanol (99.5%) and glacial acetic acid were purchased from Fisher Scientific (Pittsburgh, Pa.). All reagents were from Sigma-Aldrich (St. Louis, Mo., USA) unless otherwise specified. Standard glycans, Maltotetraose (DP4, 689.57 Da, mono-Na$^+$), maltopentose (DP5, 851.26 Da, mono-Na$^+$), maltohexanose (DP6, 1013.31 Da, mono-Na$^+$), and maltoheptaose (DP7, 1175.37 Da, mono-Na$^+$) were dissolved in HPLC grade water to 10 mM mixture.

Synthesis of aldehyde-reactive tags (iARTs). N-hydroxysuccinimide ester (16 mg), monotritylethylenediame (19 mg, Sigma), and triisopropylamine (17 μL) were added into 250 μL dichloromethane (DCM). After 2 hours, the reaction mixture was washed with saturated sodium bicarbonate solution (750 μL) twice and water (750 μL) three times. After the organic layer was dried by anhydrous sodium sulfate, the solvent was removed by Rotavapor (Buchi, Switzerland) to give 25 mg white solid. A mixture of 10% trifluoroacetic acid, 2% triisopropylsilane in DCM was added and left at room temperature for 2 h. The solvent was removed by Rotavapor. The residue was resuspended in 500 μL water and washed with ether (750 μL) three times. The aqueous layer was lyophilized to provide 12 mg iARTs containing a primary amine group for glycan labeling.

N-glycans isolation from HIV gp120. Human immunodeficiency virus (HIV) glycoprotein gp120 (100 μg; Sino Biological Inc.; Beijing, China) was dissolved in 90 μL of pH 10.0 buffer consisting of 40 mM sodium citrate and 20 mM sodium carbonate (Sigma-Aldrich). Glycan preparation via solid-phase glycan extraction (SPGE) follows protocol described above. Briefly, gp120 (100 μg in 90 μL H$_2$O) was mixed with 10 μL of 10× denaturing buffer (400 mM DTT and 5% SDS) followed by incubation at 100° C. for 10 minutes. AminoLink resin (200 μL) was loaded onto snap-cap spin-column, centrifuged at 2000 g for 1 minute. Buffer exchange was performed by adding 400 μL of pH 10.0 buffer, centrifugation at 2000 g and repeat twice. The denatured gp120 (100 μL) was loaded onto AminoLink resin in snap-cap spin-column after capped. Sodium citrate (100 mM) and sodium carbonate (50 mM) buffer (300 μL, pH 10.0) were added to spin-column for final volume of 400 μL. Sample-resin mixture was incubated at room temperature at least 4 hours with head-to-toe mixing. The mixture was centrifuged at 2000 g to remove supernatant and the resin was rinsed by 1×PBS buffer (Sigma-Aldrich; pH 7.4; 400 μL) three times. PBS buffer in the presence of 50 mM sodium cyanoborohydride (400 μL) was added to resin (spin-column capped during each incubation step). After another four hour incubation, supernatant was removed via centrifugation (2000 g) and 400 μL of 1 M Tris-HCl (pH 7.6) in the presence of 50 mM sodium cyanoborohydride was added to block un-reacted aldehyde sites of resin. The blocking process is terminated at 30 minutes. After washed by 1M sodium chloride and water twice, 2 μL of PNGase F in the presence of 1× G7 reaction buffer and 1% NP40 was added to water for a final volume of 80 μL. PNGase F enzymatic digest was conducted at 37° C. for at least 2 hours. The N-glycans released from glycoproteins were purified over Carbograph columns (Extract-Clean SPE Carbo 150 mg; Grace Division Discovery Science; Deerfield, Ill.) and eluted in 0.1% TFA 50% acetonitrile/water (1500 μL). Glycan Carbograph purification followed.

N-linked glycan labeling. The dried gp120 glycans were re-suspended in 100 μL of solution mixture consisting of dimethyl sulfoxide (DMSO) and acetic acid (AA) (70:30, vol). After complete mixing by vortex, glycans in DMSO-AA (100 μL) was aliquoted equally to two vials. One vial was added 100 μL/100 mM of iARTs[114] and the second vial added 100 μL/100 mM of iARTs[115]. Equal volume of DMSO-AA in the presence of 100 mM sodium cyanoborohydride was added to each sample. Both vials were placed in temperature-controlled microwave at 50% of power for 20 minutes (Temperature was set to 60° C.; EMS-820; Electron Microscopy Sciences; Hatfield, Pa.).

The labeled samples were mixed, which contain 114 and 115 iARTs-gp120 glycans, un-reacted iARTs, sodium cyanoborohydride, DMSO and AA. To remove non-glycan molecules, samples were purified over Carbograph column. Cleaned samples were eluted by adding 1500 μl of 0.1% formic acid in 50% ACN. The elution was dried in Speed-Vac at room temperature and re-suspended in 50 μl water.

MS Analysis. One μl of labeled glycans and one μl of DHB-DMA were deposited on μFocus MALDI plate and analyzed by Shimadzu MALDI-MS (Shimazu Corporation; Columbia, Md.) at power of 100. Data was acquired after 200 profiles at 100 different locations. For each peak, MS/MS was conducted for glycan structure identification (collision energy setting: 180-250). Further necessary MS' fragmentation is performed on those structures which cannot be determined at MS/MS level. For Orbitrap-MS/MS, ten μl of labeled gp120 glycans was diluted in 90 μl of 0.1% TFA, which was directly injected into Orbitrap (Velos Pro Mass Spectrometer; Thermo Fisher Scientific Inc.; Waltham, Mass.) through a 100-μl of needle. Flow rate was set to 2 μl/minute and each test was run for 10 minutes. The instrument was operated in data-dependent mode with m/z ranging from 300-2000 Da, in which a full MS scan (mass resolution=60,000) was followed by ten MS/MS scans. The normalized collision energy of higher energy collisional dissociation was 40%, and the dynamic exclusion duration was 5 minutes. Ions without assigned charge states were rejected for MS/MS analysis. The heated capillary was maintained at 200° C., while the ESI voltage was maintained at 2.2 kV. Each sample was analyzed in triplicate on Orbitrap.

Glycan Data Analysis. Glycan data from MS and MS' were analyzed by a suite of software tools. First, a list of glycans was calculated containing multiple HexNAc, Hexose, Sialic acid, and Fucose. The accurate mass of each possible glycan was compared with MS data from MALDI. Second, the potential structures from our list were determined by comparing the glycan mass with those in the N-glycan database we previously identified, in which the matched glycan structure could be achieved. Third, those structures were used as input for GlycoWorkbench, which is able to perform virtual MS/MS fragmentation. The virtual MS fragmentation was verified by MALDI-MS/MS data Example 1

The iARTs labeling strategy. The molecular structure of an embodiment of a pair of 2-plex iARTs is illustrated in FIG. 3, which comprises three parts, including a reporter, a balancer and a primary amine group. The reporter group in this embodiment is $C_7H_{16}{}^{14}N$ and $C_7H_{16}{}^{15}N$, thus molecular weight is 114 and 115 in MS/MS spectra respectively. This mass difference is compensated by the balance group: one carbon uses $^{13}C$ in iARTs[114] whose reporter ion is 114 Da; while the same carbon is a $^{12}C$ in iARTs[115] (FIG. 3A).

Reductive amination has been widely used to label reduce ends of glycans with different fluorophore tags. Typically, reductive amination is performed at 65° C. for 3-4 hours, or 70° C. for 2 hours, or 80° C. for 30 minutes. Studies showed that labeling glycans in high temperature (80° C.) and low pH (2 M acetic acid) for 3 hours resulted in acid catalyzed loss of sialic acids. To prevent sialic acid hydrolysis during reductive amination, temperature-controlled microwave was used to irradiate and accelerate glycan labeling for 20 minutes. The temperature was kept at 60° C. and the power of the microwave was 50%. No distinguishable difference was observed for labeling under this short incubation condition and a prolonged overnight incubation at 60° C.

Isobaric labeled glycans using iARTs are shown in FIG. 3A. The reporters can be fragmented from the balancer by using a hybrid HCD acquisition in Orbitrap, generating singly positive-charged ions at 114 and 115. Glycan quantification by iARTs is illustrated in FIG. 3B. Glycans from different sources for quantitative comparison are first labeled by iARTs[114] and iARTs[115] respectively, pooled together and purified to remove non-glycan species. The iARTs labeled glycans were then analyzed by MS/MS with the intensity of reporter ions representing the relative abundance of original samples.

The labeling efficiency was first studied using different ratio of iARTs over a mixture of four standard glycans (DP4, DP5, DP6 and DP7) at a concentration of 1 mM. The same amount of glycan was applied (10 μl at 1 mM) and iARTs was added at a ratio of 0.1, 1, 10, 50, 75 and 100 (iARTs/glycan; molar ratio). The reaction was carried out in a microwave reactor and the resulting sample was purified by Carbograph column. MALDI-MS was performed to determine the completeness of labeling. As shown in FIG. 4, negligible amount of iARTs-glycans was observed at the ratio below 10 (FIG. 4B), while labeled glycans were significantly increased with addition of more iARTs. Most glycans were labeled when the iARTs labeling reagent was 100-fold over glycans (FIG. 4A). Therefore, we used this condition for iARTs-glycan labeling thereafter.

Example 2

The effectiveness of glycan quantification by iARTs labeling may be determined by its MS and MS/MS pattern. Ideally, one would expect to observe reporter ion and glycan fragments in MS/MS spectra. Fragmentation between the reporter and the balancer leads to the detection of reporter ion 114 or 115; fragmentation of glycosidic bonds generates a series of species consisting of glycan structural information. The single charged fragment ions ($[M+H]^+$) of iARTs-labeled DP5 consist of reporter ion 114 or 115, monosaccharide-iARTs (438.29 Da), disaccharide-iARTs (600.31 Da), trisaccharide-iARTs (762.23 Da), and tetrasaccharide-iARTs (924.12 Da) (FIG. 5A). It was also noted that no other fragment ions generated from glycans overlap with reporter ions 114 and 115. Therefore, the fragments from MS/MS provide not only structural information for glycan identification, but also intensity of reporter ions for glycan quantification.

For MS analysis, it is crucial to identify how many charges a label glycan has and what adduct ions it carries. iARTs-labeled glycans usually carry one or two positive charges, including $[M+H]^+$, $[M+2H]^{2+}$, and $[M+Na]^+$, depending on ionization methods. As a result, we observed different mass spectra for the same sample using ESI-LTQ-Orbitrap or MALDI-MS as shown in FIGS. 4A and 5B. All labeled glycans are singly charged with a sodium ion in MALDI (FIG. 4); glycans are doubly charged with two protons in Orbitrap (FIG. 5B), even though we did observe small amount of singly charged glycans (<5%). The observed m/z values of four labeled glycans of DP4, DP5, DP6, and DP7 were 945.74, 1107.88, 1270.02, 1432.16 Da in MALDI spectra; while they were 462.37, 543.44, 624.51 and 705.58 Da respectively in ESI-LTQ-Orbitrap spectra. The respective ions were chosen as precursors for MS/MS quantification in Orbitrap. HCD MS/MS fragmentation of iARTs-DP5 is given in FIG. 5C. MS/MS of iARTs-DP5 consists of single-charge $Y^+$ ion, such as 924.12, 762.23, 600.31 and 438.29 Da, and double-charge $Y^{2+}$ ion, such as 462.06, 381.55, 300.16, 219.64 Da (FIG. 5C). Noticeably, the reporter ions are dominant in the spectrum, in contrast to weak peaks generated from TMT-labeled glycans. This easy fragmentation of iARTs is a significant advantage over other isobaric tags such as TMT and iTRAQ in term of quantifying glycans.

Example 3

Quantification of isobarically labeled glycans. The accuracy and dynamic range of isobaric iARTs labeling on glycans was assessed with standard glycans having free reducing ends. Four standard glycans (DPs) were labeled by iARTs114 or iARTs115. The reaction was conducted in microwave as described in experimental section. After Carbograph purification and vacuum dried, differentially labeled glycans were dissolved in water (Table 1) and pooled together. Several ratios of iARTs[114] vs. iARTs[115] were mixed, including 1:4, 1:3, 1:2, 4:1, and 10:1. One μL of each sample was used for MALDI (MS and MS/MS), while each sample was diluted to 10-fold for Orbitrap MS/MS quantification.

TABLE 1

Sample preparation for iARTs-DP labeling. Concentration of iARTs-114 and iARTs-115 is 50 mM; DP (DP4, DP5, DP6 and DP7) is 100 μM

| Ratio | iARTs[114]-DP | | iARTs[115]-DP | | Dissolved in DI after purification (μL) |
|---|---|---|---|---|---|
| | iARTs[114] (μL) | DP (μL) | iARTs[115] (μL) | DP (μL) | |
| 1:4 | 10 | 50 | 40 | 200 | 250 |
| 1:3 | 10 | 50 | 30 | 150 | 200 |
| 1:2 | 10 | 50 | 20 | 100 | 150 |
| 4:1 | 80 | 400 | 20 | 100 | 500 |
| 10:1 | 100 | 500 | 10 | 50 | 550 |

Both MALDI-MS (FIG. 4A) and Orbitrap-MS (FIG. 6B) indicated complete labeling of glycans with iARTs. As an example shown in FIG. 5B, the pooled iARTs-DP5 with an expected ratio of 1:3 (114/115) showed the intensity ratio at 1:3.27 in ESI-LTQ-Orbitrap MS/MS. The observed ratios were plotted versus expected ratios (FIG. 6A). Overall, report ions from MS/MS spectra on iARTs-DPs show good quantification agreement with theoretical ratio and dynamic range. At an expected ratio of 10:1, the observed ratio is approximately 8.5. Clearly, iARTs is a useful tag for glycan quantification considering its labeling efficiency, report ion fragmentation, quantification accuracy and dynamic range.

Example 4

Sensitivity improvement on iARTs-glycan. It is challenging to analyze glycans by mass spectrometry due to the poor ionization efficiency. Glycans are more hydrophilic than peptides so they do not fly as well as peptides. However, the ionization of glycans can be improved by increasing its hydrophobicity via modification. iARTs are hydrophobic tags and potentially increase the ionization of labeled glycans. To test this possibility, a serial dilution was made of an iARTs-labeled DP glycan and a native DP glycan at the concentrations of 1500, 375, 150, 75, 25, 12.5 μM. Each pair of a non-labeled glycan and an iARTs-glycan at the same concentration was mixed and characterized by MALDI-MS for comparison of ionization efficiency. Intensity of individual glycan versus their concentration was then plotted as shown in FIGS. 7A and 7B. iARTs-glycan exhibited better ionization efficiency, whose intensity is approximately five-fold (DP5) and two-fold (DP6) over respective non-labeled glycans. The difference was more prominent at lower concentrations. The MALDI-MS spectra on 25 μM of DP6 versus iARTs-DP6 (FIG. 7B) clearly demonstrate this pattern, in which DP6 was hardly detectable at this concentration (FIG. 7 (B)) while iARTs-DP6 was evident with high signal-to-noise ratio (>>10) (FIG. 5 (B)). This feature is extremely useful for glycan identification and quantification by mass spectrometry.

Example 5

HIV gp120 glycan quantification. The glycoprotein 120 subunit (gp120) is an important part of the envelope spikes that decorate the surface of HIV and a major target for neutralizing antibodies. It has been recognized that the outer domain of gp120 is largely covered by glycans which present as weak immunogenic antigens. In addition, glycans on gp120 render the underlying protein surface invisible to the immune system. It was reported that gp120 contains high-mannoses and many other complex/hybrid glycans.

The structures of these glycans are quite sensitive to environments and could be completely different on wild type (WT) and mutant. Even the same glycans can display different relative abundance under various conditions. Therefore, it is important to identify and profile glycans of gp120 as this information can provide novel targets for HIV vaccines.

Glycans from gp120 (100 μg) was dissolved in 100 μL of water. Two 20 μL aliquots of glycans were placed in two microcentrifuge tubes and dried in vacuum, followed by dissolving in 20 μL of DMSO-acetic acid solution. Equal amount of GP120 glycans from HIV were then labeled with iARTs. One tube of glycans was labeled with iARTs[114] and the other labeled with iARTs[115]. After labeling processes as described previously, both samples were pooled and purified by Carbograph. Samples were re-suspended in 40 μL of water in the presence of 0.1% TFA after vacuum dried. MALDI-MS spectra showed that thirty-three labeled glycans were detected (FIG. 8) and spiked DP7 indicated complete labeling of glycans. The identified high-mannose and hybrid/complex glycans are listed in Table 2 (corresponding glycan structures are given in FIG. 8). It was noted that the quantitative ratios were quite close to the expected values for small glycans, but show significant deviation for glycans with molecular weight more than 1500 Da. This is caused by the different energy requirement for the fragmentation of iARTs and glycans with different size. Even through iARTs is easier to fragment than other isobaric tags (e.g. TMT and iTRAQ), it still needs higher collision energy than glycosidic bonds. In small glycans, there are few glycosidic bonds to break apart so strong reporter ions can be obtained to provide reliable quantification results. With the size of glycans increasing, the intensity of reporter ions becomes lower, which compromises the accuracy of quantification. To alleviate this problem, further fragmentation (MS3) of fragment glycans from MS/MS containing the iARTs can be used for quantitation (FIG. 6B).

Isobaric iARTs are capable of quantifying gp120 glycans for relative abundance. As shown in Table 2, we mixed a ratio of 1:1 of gp120 glycans labeled by iARTs[114] and iARTs[115]. The doubly-charged ions listed in Table were detected in Orbitrap HCD. No sodium adducts of glycans were observed in Orbitrap. The singly-charged ions listed in the same table were observed in MALDI-MS, which contain a sodium ion. The MALDI-MS spectra can clearly connected to those peaks observed in Orbitrap for quantification analysis. We determined the reproducibility of quantifying gp120 glycans with a CV less than 25% for glycans less than 2000 Da.

TABLE 2

Quantification of iARTs labeled glycans using Orbitrap. Glycans were extracted from gp120 glycoprotein via solid-phase glycan extraction (SPGE). (*Structures of these glycans have not been assigned, yet their MS/MS spectra indicate that they are glycans.)

| Labeled glycans (2H+, Da) | Labeled Glycans (Na+, Da) | Native Glycans (Na+, Da) | Observed Ratio (114/115) | Standard Deviation (±) | Expected Ratio | %, error |
|---|---|---|---|---|---|---|
| 623.29* | 1267.58 | 1012.58 | 1.119 | 0.084 | 1 | 11.9 |
| 643.38* | 1307.76 | 1052.76 | 0.976 | 0.041 | 1 | 2.4 |
| 655.38 | 1331.76 | 1076.76 | 1.155 | 0.035 | 1 | 15.5 |
| 674.94* | 1370.88 | 1115.88 | 1.173 | 0.391 | 1 | 17.3 |
| 705.81 | 1432.62 | 1177.62 | 0.636 | 0.015 | 1 | 36.4 |
| 717.96* | 1456.92 | 1201.92 | 1.051 | 0.115 | 1 | 5.1 |
| 737.83* | 1496.66 | 1241.66 | 0.856 | 0.078 | 1 | 14.4 |

TABLE 2-continued

Quantification of iARTs labeled glycans using Orbitrap. Glycans were extracted from gp120 glycoprotein via solid-phase glycan extraction (SPGE). (*Structures of these glycans have not been assigned, yet their MS/MS spectra indicate that they are glycans.)

| Labeled glycans ($2H^+$, Da) | Labeled Glycans ($Na^+$, Da) | Native Glycans ($Na^+$, Da) | Observed Ratio (114/115) | Standard Deviation (±) | Expected Ratio | %, error |
|---|---|---|---|---|---|---|
| 743.39 | 1512.32 | 1257.32 | 0.897 | 0.067 | 1 | 10.3 |
| 757.41 | 1535.82 | 1280.82 | 0.836 | 0.158 | 1 | 16.4 |
| 773.32* | 1567.64 | 1312.64 | 0.921 | 0.373 | 1 | 7.9 |
| 807.50* | 1636.26 | 1381.26 | 0.849 | 0.360 | 1 | 15.1 |
| 818.85 | 1658.70 | 1403.70 | 0.766 | 0.127 | 1 | 23.4 |
| 824.52 | 1670.04 | 1419.04 | 1.111 | 0.877 | 1 | 11.1 |
| 831.37* | 1683.74 | 1428.74 | 1.023 | 0.371 | 1 | 2.3 |
| 838.54 | 1698.08 | 1443.08 | 1.085 | 0.532 | 1 | 8.5 |
| 841.02* | 1703.04 | 1448.04 | 0.847 | 0.547 | 1 | 15.3 |
| 859.88 | 1740.76 | 1485.76 | 0.772 | 0.194 | 1 | 22.8 |
| 862.38* | 1745.76 | 1490.76 | 0.707 | 0.251 | 1 | 29.3 |
| 868.55 | 1758.10 | 1503.10 | 0.565 | 0.120 | 1 | 43.5 |
| 888.5 | 1798.00 | 1543.00 | 0.620 | 0.390 | 1 | 38.0 |
| 899.88 | 1820.76 | 1565.76 | 0.793 | 0.657 | 1 | 20.7 |
| 903.89* | 1828.78 | 1573.78 | 0.610 | 0.333 | 1 | 39.0 |
| 926.56* | 1874.12 | 1619.12 | 0.961 | 0.547 | 1 | 3.9 |
| 932.91* | 1886.82 | 1631.82 | 0.321 | 0.498 | 1 | 67.9 |
| 940.91 | 1902.82 | 1647.82 | 0.633 | 0.209 | 1 | 36.7 |
| 949.43 | 1919.86 | 1664.86 | 0.581 | 0.078 | 1 | 41.9 |
| 953.42* | 1927.84 | 1672.84 | 0.499 | 0.343 | 1 | 50.1 |
| 1013.94 | 2048.88 | 1793.88 | 0.404 | 0.245 | 1 | 59.6 |
| 1025.43* | 2071.86 | 1816.86 | 0.689 | 0.096 | 1 | 31.1 |
| 1034.45 | 2089.90 | 1834.90 | 0.287 | 0.155 | 1 | 71.3 |
| 1042.95 | 2106.90 | 1851.90 | 0.530 | 0.375 | 1 | 47.0 |
| 1086.45* | 2193.90 | 1938.90 | 0.356 | 0.143 | 1 | 64.4 |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. In accordance with an embodiment, the present invention provides an iART ligand comprising:
   a) a reporter group comprising a $C_1$-$C_{10}$ alkyl moiety having a primary amine group which can be optionally a $^{15}N$ labeled amine;
   b) a balance group consisting of —$CONHCH_2CH_2CONHCH_2CH_2NH$—, wherein the first carbon can optionally be $^{13}C$; and when the amine is labeled, the first carbon is not labeled, and when the first carbon is labeled, the amine is not labeled, and said ligand can covalently linked to a glycan.

2. The iART ligand of claim 1, having the following formula:

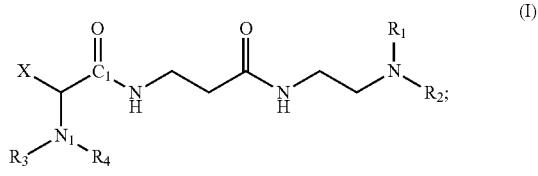

wherein $R_1$ to $R_4$ can be independently H, $C_1$-$C_6$ alkyl, or $C_1$-$C_6$ alkenyl;
$N_1$ is $^{14}N$ or $^{15}N$;
$C_1$ is $^{12}C$ or $^{13}C$; and
X is a $C_1$-$C_{10}$ alkyl group.

3. The iART ligand of claim 2, wherein the iART has the following formula:

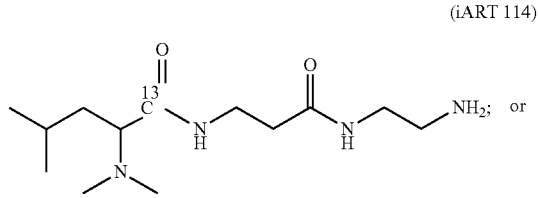
(iART 114)

or

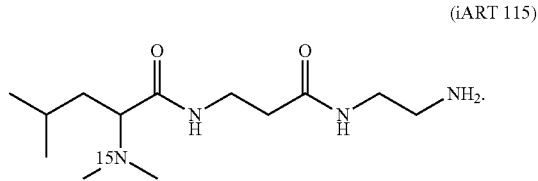
(iART 115)

* * * * *